United States Patent
Looper et al.

(10) Patent No.: US 10,799,263 B2
(45) Date of Patent: Oct. 13, 2020

(54) CATHETER DESIGN FOR USE IN TREATING PLEURAL DISEASES

(75) Inventors: Anthony Looper, Lake Zurich, IL (US); John A. Krueger, Muskego, WI (US); Jeffrey Schmitt, Trumbull, CT (US)

(73) Assignee: CAREFUSION 2200, INC., San Diego, CA (US)

( * ) Notice: Subject to any disclaimer, the term of this patent is extended or adjusted under 35 U.S.C. 154(b) by 7 days.

(21) Appl. No.: 13/696,555

(22) PCT Filed: May 6, 2011

(86) PCT No.: PCT/US2011/035545
§ 371 (c)(1),
(2), (4) Date: Apr. 29, 2013

(87) PCT Pub. No.: WO2011/140456
PCT Pub. Date: Nov. 10, 2011

(65) Prior Publication Data
US 2013/0204279 A1 Aug. 8, 2013

Related U.S. Application Data

(60) Provisional application No. 61/332,547, filed on May 7, 2010.

(51) Int. Cl.
*A61B 17/3207* (2006.01)
*A61M 25/00* (2006.01)
*A61M 16/04* (2006.01)

(52) U.S. Cl.
CPC ..... *A61B 17/3207* (2013.01); *A61M 16/0406* (2014.02); *A61M 25/0068* (2013.01);
(Continued)

(58) Field of Classification Search
CPC ........ A61B 17/3207; A61B 17/320708; A61B 17/320725; A61B 17/32075;
(Continued)

(56) References Cited

U.S. PATENT DOCUMENTS

| 4,830,615 A | * | 5/1989 | Feinman | A61C 3/06 433/142 |
| 5,545,132 A | | 8/1996 | Fagan et al. | |

(Continued)

FOREIGN PATENT DOCUMENTS

| CA | 2 557 222 A1 | 9/2005 |
| CN | 2201117 Y | 6/1995 |

(Continued)

OTHER PUBLICATIONS merriam-webster.com, catheter definition; retrieved May 27, 2015.*
(Continued)

*Primary Examiner* — Tan-Uyen T Ho
*Assistant Examiner* — Chima U Igboko
(74) *Attorney, Agent, or Firm* — Arent Fox LLP

(57) ABSTRACT

A catheter for use in treating pleura diseases, such as pleural effusions and pneumothorax, includes a tip portion that is configured to irritate the pleura when the catheter is inserted in the pleural cavity, thereby initiating mechanical pleurodesis. The tip portion has a substantially rough configuration and may include one or more protrusions that contact the pleura when the catheter is in use, thereby irritating the layers. This irritation causes the creation of fibrous adhesions between the parietal and visceral layers that close off the pleural cavity and prevent further fluid and/or air accumulations that occur as a result of pleural diseases.

21 Claims, 5 Drawing Sheets

(52) U.S. Cl.
CPC ............... *A61M 2025/006* (2013.01); *A61M 2025/0096* (2013.01); *A61M 2210/101* (2013.01)

(58) Field of Classification Search
CPC . A61B 2017/320733; A61B 2017/003; A61M 2210/101; A61M 25/0067; A61M 25/0068; A61M 25/0082; A61M 2025/006; A61M 2025/0096; A61M 16/0404
USPC ............................................................ 606/159
See application file for complete search history.

(56) References Cited

U.S. PATENT DOCUMENTS

| | | | |
|---|---|---|---|
| 6,921,396 B1 | 7/2005 | Wilson et al. | |
| 8,163,034 B2* | 4/2012 | Chang et al. | 623/23.72 |
| 2003/0187491 A1 | 10/2003 | Greenberg et al. | |
| 2004/0073259 A1* | 4/2004 | Munzer | A61N 1/403 607/1 |
| 2004/0181251 A1* | 9/2004 | Hacker | A61B 17/32002 606/170 |
| 2005/0015107 A1* | 1/2005 | O'Brien | 606/194 |
| 2005/0245846 A1* | 11/2005 | Casey | A61M 25/0127 600/585 |
| 2006/0009801 A1* | 1/2006 | McGurk et al. | 606/214 |
| 2006/0124126 A1* | 6/2006 | Tanaka | 128/200.26 |
| 2006/0287669 A1* | 12/2006 | Casey et al. | 606/200 |
| 2007/0015107 A1* | 1/2007 | Mannschedel | A61C 5/42 433/102 |
| 2007/0066972 A1* | 3/2007 | Ormsby | A61B 18/1492 606/41 |
| 2007/0078442 A1 | 4/2007 | Mayse | |
| 2007/0135830 A1* | 6/2007 | Schaeffer | 606/192 |
| 2007/0163598 A1* | 7/2007 | Chang et al. | 128/207.16 |
| 2007/0239109 A1* | 10/2007 | Dereuil | 604/96.01 |
| 2007/0241119 A1* | 10/2007 | Durkin | A61M 39/02 221/2 |
| 2007/0282359 A1* | 12/2007 | Tal | 606/159 |
| 2008/0071341 A1* | 3/2008 | Goode et al. | 607/122 |
| 2008/0221566 A1* | 9/2008 | Krishnan | A61B 17/0057 606/41 |
| 2008/0319455 A1* | 12/2008 | Harris | A61B 17/0684 606/139 |
| 2009/0099583 A1 | 4/2009 | Butterfield et al. | |
| 2009/0205643 A1* | 8/2009 | Tanaka | A61M 1/04 128/200.24 |
| 2010/0204707 A1* | 8/2010 | Tanaka et al. | 606/108 |

FOREIGN PATENT DOCUMENTS

| | | |
|---|---|---|
| EP | 0 384 476 A1 | 8/1990 |
| JP | 2006/142028 A | 6/2006 |
| WO | WO 2009/060322 A2 | 5/2009 |
| WO | WO 2009/105473 A9 | 8/2009 |

OTHER PUBLICATIONS

Definition: Catheter; http://www.dictionary.com/browse/catheter; Jul. 20, 2017; catheter_definition.pdf.*
Chinese Office Action, Chinese Application No. 201180022936.9, dated Apr. 3, 2012.
Russian Office Action dated Mar. 24, 2015 issued in Russian Patent Application No. 2012153206.
Canadian Office Action issued in corresponding Canadian Patent Application No. 279843 dated Feb. 27, 2018.
Korean Office Action issued in Korean Patent Application No. 10-2012-7032184 dated Jan. 30, 2019.
Indian Office Action dated Jun. 21, 2019 issued in Indian Application No. 10437/DELNP/2012.

* cited by examiner

CATHETER DESIGN FOR USE IN TREATING PLEURAL DISEASES

CROSS REFERENCE TO RELATED APPLICATION

This application is a National Stage entry of International Application PCT/US2011/035545, filed May 6, 2011, which claims priority to U.S. Patent Application No. 61/332,547, filed May 7, 2010, the disclosure of the prior applications are hereby incorporated in their entirety by reference.

FIELD OF THE INVENTION

The present invention relates to an improved catheter design for use in treating pleural diseases.

BACKGROUND OF THE INVENTION

The pleural cavity and the pleura serve an important function of aiding in the optimal functioning of the lungs during respiration. Diseases affecting the pleural cavity and pleura include pleural effusions and pneumothorax. Pleural effusions involve the build-up of fluid around the lungs. Pleural effusions can be associated with conditions such as cancer, tuberculosis, congestive heart failure, pneumonia, pulmonary emboli, viral disease, cirrhosis, post coronary artery bypass graft surgery, gastrointestinal disease, tuberculosis, and mesothelioma. Pneumothorax occurs when air or gas is present in the pleural cavity.

Patients with pleural diseases such as symptomatic pleural effusions or pneumothorax are typically treated with thoracentesis to remove fluid or air, and/or chemical or mechanical pleurodesis. Pleurodesis involves irritation of the parietal and/or visceral layers of the pleura to close off the pleural cavity and prevent further fluid and/or air accumulations. Pleurodesis is typically characterized by the creation of fibrous adhesions between the parietal and visceral layers of the pleura.

Mechanical pleurodesis can be achieved, for example, with the insertion of a rough pad or a catheter into the pleural cavity. Catheters are used in many medical procedures and are typically inserted into a patient's body cavity, duct, or vessel. Catheters are typically used to drain fluids, inject fluids, and to provide access for surgical instruments into or from a body cavity. Catheters may allow a user, such as a doctor, nurse, or other medical professional, to access a specific portion of a patient's body without making invasive incisions.

When using a catheter to perform mechanical pleurodesis, the tip of the catheter may be used to irritate the parietal and/or visceral layers of the pleura, thereby causing the creation of fibrous adhesions between the parietal and visceral layers. Typical catheters, however, are not highly effective in adequately irritating the parietal and visceral layers because they are substantially smooth.

Thus, there is a need in the art for an improved catheter design for use in treating pleural diseases.

SUMMARY OF THE INVENTION

The present invention provides a catheter for use in treating pleural diseases, such as pleural effusions and pneumothorax. The catheter may be inserted within the pleural cavity of a patient's lungs for initiating mechanical pleurodesis. The catheter includes a tip portion that is configured to irritate the pleura when the catheter is inserted in the pleural cavity. This irritation causes the creation of fibrous adhesions between the parietal and visceral layers that close off the pleural cavity and prevent further fluid and/or air accumulations that occur as a result of pleural diseases.

Other novel features and advantages of the present invention will become apparent to those skilled in the art upon examination of the following or upon learning by practice of the invention.

DETAILED DESCRIPTION OF THE INVENTION

Figure 1:
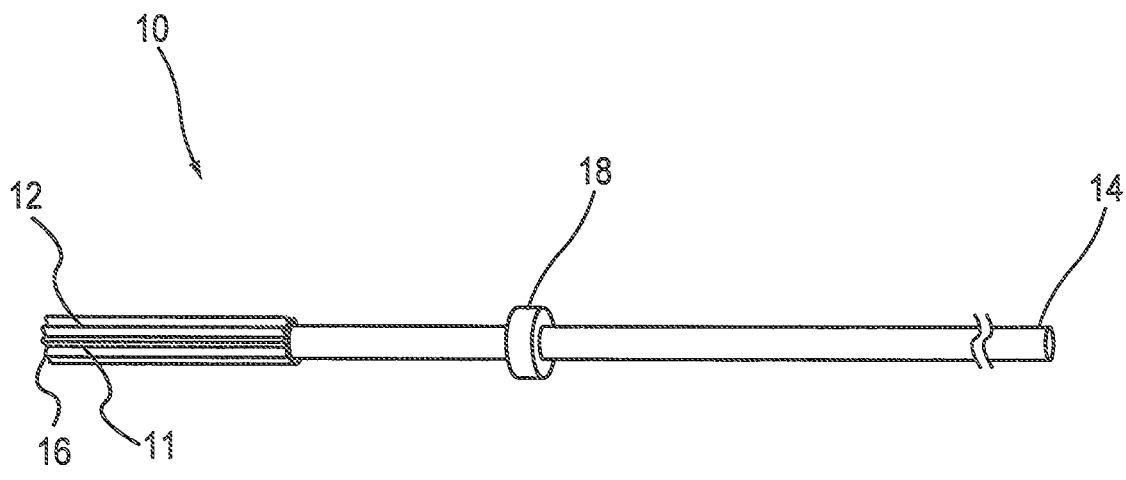
FIG. 1 shows a catheter according to an embodiment of the invention.

The present invention provides a catheter for use in treating pleural diseases, such as pleural effusions and pneumothorax. The catheter may be inserted within the pleural cavity of a patient's lungs for initiating mechanical pleurodesis. The catheter includes a tip portion that is positioned toward its distal end that is configured to irritate the pleura when the catheter is inserted in the pleural cavity. This irritation causes the creation of fibrous adhesions between the parietal and visceral layers that close off the pleural cavity and prevent further fluid and/or air accumulations that occur as a result of pleural diseases.

The surface of the tip portion has a substantially rough configuration that is capable of irritating the pleura when the catheter is inserted in the pleural cavity. The tip portion's surface may include one or more protrusions that contact the pleura when the catheter is in use, thereby irritating the layers.

The roughness of the tip portion may be varied to achieve a desired degree of irritation of the pleura based on a patient's condition. In general, a catheter tip portion having a roughness of about 50 to about 600 microinches, measured according to the ANSI B46.1-2002 Surface Texture Standard is desirable to initiate pleurodesis.

The shape, size, and arrangement of the protrusions may be varied to achieve a catheter tip surface with the desired roughness. The protrusions may be of any shape, size, and arrangement that can effectively irritate the pleura to initiate pleurodesis. For example, the cross-section of a protrusion may be polygonal, such as triangular, rectangular, or other polygonal. Alternatively, the cross-section of a protrusion may be substantially curved, such as circular, semi-circular or elliptical. In addition, any combination of cross-sections of protrusions may be used in a single catheter.

The size of the protrusions may be varied depending on the degree of irritation of the pleura desired. Typically, larger protrusions result in a higher degree of irritation in the pleura than do smaller protrusions. The protrusions typically range in size from about 50 to bout 600 microinches in height measured on the surface of the catheter portion that is inserted in the pleural space. The protrusions are generally positioned near the tip portion of the catheter from about ½ to about 15 inches from the distal (inserted) end of the catheter. They may also be located at a portion of the catheter other than the tip portion, but still along a surface of the inserted portion of the catheter.

The protrusions formed near or at the tip portion of the catheter according to the present invention may be substantially uniform or irregular in size and shape. For example, the size and shape of the protrusions may be varied along the length of the tip portion of the catheter to better irritate the pleura. Larger protrusions may be present at the proximal end of the catheter, while smaller ridges may be present towards the distal end of the catheter, thereby forming a cone-shaped tip portion.

The protrusions may be arranged near or at the tip portion of the catheter in any orientation that allows the catheter to effectively irritate the pleura. In particular, the protrusions may be oriented randomly or oriented to form one or more continuous or discontinuous patterns on the surface of the catheter. For example, the protrusions may form ridges that may be substantially linear or curved. When the protrusions form a discontinuous ridge, the protrusions may appear as teeth at the tip portion of the catheter. If the catheter is oval in cross-section, the protrusions may be located on the elongated portion of the oval, and not along the curved portion of the oval, or vice versa, or on both the elongated and curved portions of the oval.

The protrusions may be oriented closely together, or there may be some space between the protrusions. Further, the density of protrusions on a tip portion's surface may be varied in a single catheter. For example, a higher density of protrusions may be present towards the distal end of the inserted portion of the catheter while a lower density of protrusions may be present towards the proximal end of the inserted portion.

The protrusions near or at the tip portion of the catheter may be formed of any material that is known in the art that is able to irritate the pleura. The material preferably has sufficient rigidity so that the protrusions are able to irritate the pleural layers. These materials may include, but are not limited to, silicone, PVC, polypropylene, polyurethane, other thermoplastic elastomers, etc.

The protrusions may be formed by any method known in the art including, but not limited to, molding, extrusion, coextrusion, overmolding, machining, etching, EDM, sputtering, vapor deposition, etc. They may also be formed by various material removal or deposition techniques. The protrusions may be formed separately from and then attached to the tip portion of the catheter, or they may be formed integrally with the tip portion of the catheter.

The catheter of the invention may be used to initiate pleurodesis by inserting the distal end of the catheter into the pleural cavity and contacting the protrusions at or near the distal tip portion of the catheter with the pleura. This contact between the protrusions and the pleura irritates the pleura, thus initiating pleurodesis. The contact may be achieved by the natural movement of the catheter positioned in the pleural space, or by a more active method such as by an external movement, agitation, or force such as a wire that is inserted through the catheter, a magnet that acts on the catheter, etc.

Any shape, size, or style of catheter that is known in the art may be used in the present invention. The catheter typically has a circular cross-section, but it may be of any other shape including, but not limited to, oval, elliptical, triangular, rectangular, or other polygonal. The catheter may be flexible or rigid and may be made of any material that is known in the art. For example, the catheter may be made of a polymer, such as silicone, that is inert and unreactive to body fluids and a range of medical fluids with which it may come into contact, or other materials that are known to have at least a mildly irritating effect on human tissues or cells.

The catheter of the invention may optionally include fenestrations, which allow fluid from a patient's body cavity to pass through them, thereby removing the fluid from the cavity towards a center lumen. The size of the fenestrations may vary, but they are typically of a size sufficient to allow bodily fluids to pass through them without clogging. The fenestrations may be arranged randomly or in a specified pattern.

The catheter may also include a cuff that assists in positioning the catheter in a patient's body cavity and in surrounding tissues and may reduce the occurrence of infection by creating a seal that prevents external microorganisms from penetrating and infecting the pleural space. The cuff may be made of any suitable material that is commonly used in catheters including, but not limited to, polyester.

An example of a catheter according to an embodiment of the invention is shown in FIG. 1. The catheter 10 includes a distal end 12 and a proximal end 14. A tip portion 16 is positioned towards or at the distal end 12 and includes protrusions 11. The proximal end 14 may be joined to a drainage container or other medical device. The catheter 10 may include a cuff 18.

According to an embodiment of the invention, a catheter of any cross-section includes a tip portion towards or at its distal end that has one or more protrusions of any size or shape. The protrusions may be positioned on a surface of the tip portion of the catheter.

Figure 2A:
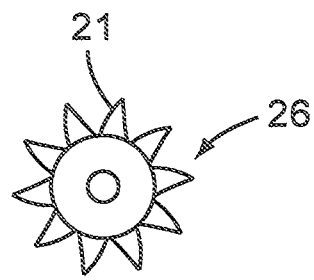
FIG. 2a is a cross-sectional view of a tip portion of a catheter according to an embodiment of the invention.

An example of a tip portion with protrusions according to this embodiment is shown in FIG. 2*a*. In FIG. 2*a*, the tip portion 26 includes a plurality of protrusions 21, which have a triangular cross-section, that are positioned on the surface of the catheter, which has a circular cross-section.

Figure 2B:
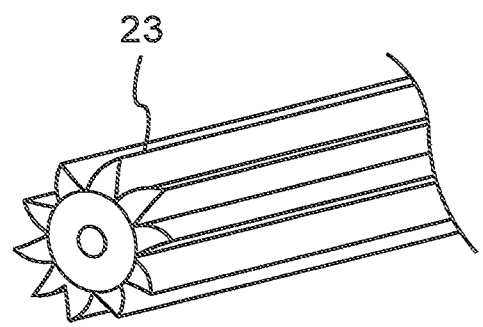
FIG. 2b is angled view of a tip portion of a catheter according to an embodiment of the invention.
Figure 2C:
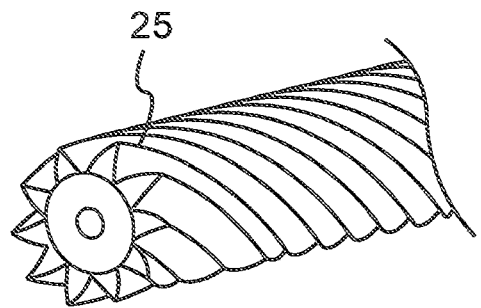
FIG. 2c is angled view of a tip portion of a catheter according to another embodiment of the invention.

According to an embodiment of the invention, protrusions of any size or shape are arranged in a pattern on a surface of the tip portion of the catheter of any cross-sectional shape. For example, the pattern may include one or more continuous ridges on the surface of the tip portion. The ridges may be substantially linear or curved. Examples of catheter tips according to these embodiments are shown in FIGS. 2*b* and 2*c*. FIG. 2*b* shows a tip portion that includes protrusions with triangular cross-section that form a plurality of substantially linear ridges 23 on a catheter with circular cross-section. FIG. 2*c* shows a tip portion that includes protrusions with triangular cross-section that form a plurality of curved ridges 25 on a catheter with circular cross-section.

Figure 2D:
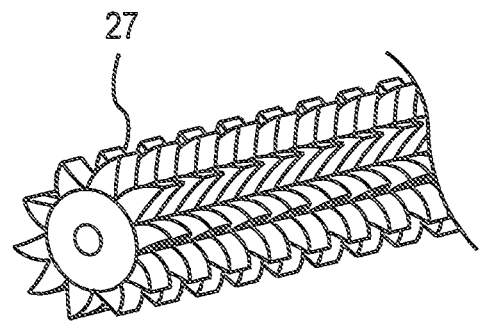
FIG. 2d is angled view of a tip portion of a catheter according to another embodiment of the invention.

According to another embodiment of the invention, the protrusions of any size or shape may be oriented to form one or more discontinuous ridges on a surface of the catheter of any cross-sectional shape. An example of a catheter according to this embodiment is shown in FIG. 2*d*. FIG. 2*d* shows a tip portion that includes protrusions with triangular cross-section that form a plurality of discontinuous ridges 27 on a catheter with circular cross-section.

Figure 3A:
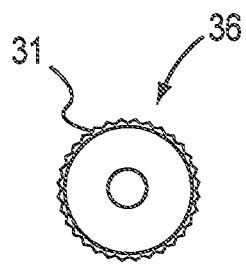
FIG. 3a is a cross-sectional view of a tip portion of a catheter according to another embodiment of the invention.
Figure 3B:
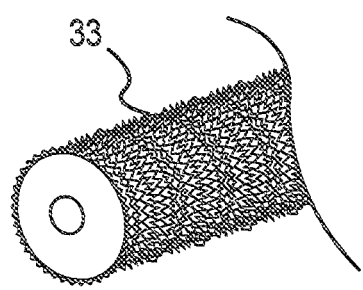
FIG. 3b is angled view of a tip portion of a catheter according to another embodiment of the invention.

According to another embodiment of the invention, one or more protrusions may be of any size or shape and be oriented randomly on a surface of the tip portion of the catheter of any cross-sectional shape. An example of a catheter according to this embodiment is shown in FIGS. 3a and 3b. FIGS. 3a and 3b shows the tip portion 36 of a catheter with a plurality of protrusions 31 that are arranged randomly.

According to another embodiment of the invention, one or more protrusions may be formed integrally with the catheter of any cross-sectional shape. The protrusions may be of any size or shape and may be arranged in any way including, but not limited to, randomly oriented or one or more continuous or discontinuous ridges that are substantially linear or curved.

Figure 4A:
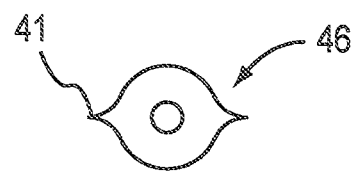
FIG. 4a is a cross-sectional view of a tip portion of a catheter according to another embodiment of the invention.
Figure 4B:
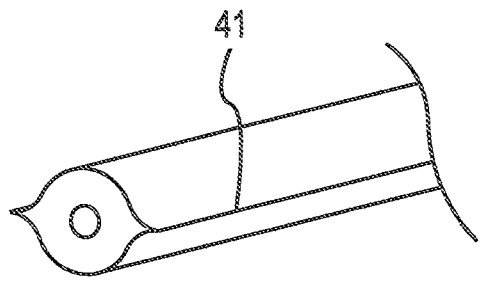
FIG. 4b is angled view of a tip portion of a catheter according to another embodiment of the invention.

An example of a catheter according to this embodiment of the invention is shown in FIGS. 4a and 4b. in FIGS. 4a and 4b, two integrally formed protrusions 41 with triangular cross-section are arranged at opposing sides of the tip portion 46 of the catheter with circular cross-section to form continuous ridges.

The catheter of the present invention may include any combination of the features described above.

Although the catheter of the present invention is described above as being useful for initiating mechanical pleurodesis to treat pleural diseases such as pleural effusions and pneumothorax, the catheter may also be used in any type of medical procedure that requires irritating or roughening a surface. In addition, the catheters may be used in conjunction with other medical instruments including, but not limited to, pleural shunts, ascetic shunts, hydro-cephalic shunts.

The invention claimed is:

1. A method of mechanical pleurodesis comprising:
    inserting a catheter into a patient's pleural cavity, the catheter comprising a lumen and an outer wall at least partially surrounding the lumen with an external surface extending from a proximal end of the catheter to an opening of the lumen at a distal most end of the catheter, wherein a tip portion of the external surface of the catheter comprises a plurality of protrusions thereon, the plurality of protrusions comprised of at least one of a silicone, polyvinyl chloride (PVC) polypropylene, polyurethane, thermoplastic elastomer, and wherein at least one of a size or shape of the plurality of protrusions are varied along a length of the tip portion such that larger protrusions are provided at a proximal end thereof and smaller protrusions are present at a distal end thereof;
    using the catheter to remove pleural fluid from the patient; and
    providing active movement to the tip portion of the catheter within the pleural cavity during use of the catheter, wherein the active movement contacts the plurality of protrusions with a pleura to perform mechanical pleurodesis.

2. The method according to claim 1 wherein the tip portion is forms a portion of the distal most end of the catheter.

3. The method according to claim 1 wherein the protrusions have a shape selected from the group consisting of circular, elliptical, triangular, rectangular, or other polygonal.

4. The method according to claim 1 wherein the protrusions are oriented randomly along the external surface of the catheter at or near the distal end of the catheter.

5. The method according to claim 1 wherein the protrusions form continuous ridges at the tip portion.

6. The method according to claim 5 wherein the continuous ridges are substantially linear.

7. The method according to claim 5 wherein the continuous ridges are curved.

8. The method according to claim 1 wherein the protrusions form discontinuous ridges at the tip portion.

9. The method according to claim 8 wherein the discontinuous ridges are curved.

10. The method according to claim 8 wherein the discontinuous ridges are substantially linear.

11. The method according to claim 1 wherein the protrusions are formed integrally with the external surface of the catheter at the tip portion.

12. The method according to claim 1 where the one or more protrusions are configured to irritate or roughen a surface.

13. The method according to claim 1 where the catheter is configured for movement within the pleural space.

14. The method according to claim 1 wherein the catheter comprises a cuff arranged between the proximal end and a distal end of the catheter.

15. The method according to claim 1 wherein a cross-section of the catheter has a shape selected from a group consisting of circular, ovular, elliptical, triangular and rectangular.

16. The method according to claim 1 wherein the catheter is formed from an inert polymer that is rigid or flexible.

17. The method of claim 1, wherein the outer wall of the catheter comprises a tubular body.

18. The method of claim 1, wherein the active movement comprises subjecting th e catheter to a force from a wire inserted through the catheter.

19. The method of claim 1, wherein movement comprises subjecting the catheter to a force from a magnet acting on the catheter.

20. A method of irritating or roughening a patient's pleura comprising the steps of:
    inserting a catheter into a patient's pleural cavity, the catheter comprising a lumen and an outer wall at least partially surrounding the lumen with an external surface extending from a proximal end of the catheter to an opening of the lumen at a distal most end of the catheter, wherein a tip portion of the external surface of the catheter comprises a plurality of protrusions thereon, and at least one of the size or shape of the plurality of protrusions are varied along a length of the tip portion such that larger protrusions are provided at a proximal end thereof and smaller protrusions are present at a distal end thereof, wherein the plurality of protrusions comprise at least one of a silicone, polyvinyl chloride (PVC), polypropylene, polyurethane, or a thermoplastic elastomer;
    using the catheter to remove pleural fluid from the patient; and
    providing active movement to the tip portion within the pleural cavity during use of the catheter, wherein the active movement contacts the protrusions at the tip portion with the pleura to irritate or roughen the pleura.

21. The method of claim 20, wherein the catheter comprises a tubular body and wherein the one or more protrusions are disposed along a length of the tubular body.

* * * * *